United States Patent
Heller et al.

(10) Patent No.: US 7,479,507 B2
(45) Date of Patent: Jan. 20, 2009

(54) ANTI-INFLAMMATORY SUBSTITUTED PHENOLS AND ELASTOMERIC COMPOSITIONS FOR ORAL DELIVERY OF DRUGS

(76) Inventors: Adam Heller, 4711 Spicewood Springs Rd., Apt. 271, Austin, TX (US) 78755;
Charles Haymore, 2143 Zercher Rd., San Antonio, TX (US) 78209-1189

( * ) Notice: Subject to any disclaimer, the term of this patent is extended or adjusted under 35 U.S.C. 154(b) by 104 days.

(21) Appl. No.: 10/542,339

(22) PCT Filed: Jan. 13, 2004

(86) PCT No.: PCT/US2004/000811
§ 371 (c)(1),
(2), (4) Date: May 15, 2006

(87) PCT Pub. No.: WO2004/064781
PCT Pub. Date: Aug. 5, 2004

(65) Prior Publication Data
US 2006/0258618 A1 Nov. 16, 2006

Related U.S. Application Data

(60) Provisional application No. 60/440,310, filed on Jan. 14, 2003.

(51) Int. Cl.
A61K 31/21 (2006.01)
(52) U.S. Cl. ........................ 514/506; 514/141; 514/517; 514/706
(58) Field of Classification Search ........................ None
See application file for complete search history.

(56) References Cited

U.S. PATENT DOCUMENTS

| | | | |
|---|---|---|---|
| 4,029,812 A | 6/1977 | Wagner et al. |
| 4,076,841 A | 2/1978 | Wagner et al. |
| 4,078,084 A | 3/1978 | Wagner et al. |
| 4,124,725 A | 11/1978 | Moore |
| 4,172,082 A | 10/1979 | Moore |
| 4,172,151 A | 10/1979 | Moore |
| 4,212,882 A | 7/1980 | Moore |
| 4,357,345 A | 11/1982 | Moore |
| 4,414,217 A | 11/1983 | Moore |
| 4,418,074 A | 11/1983 | Moore |
| 4,431,831 A | 2/1984 | Moore |
| 4,535,165 A | 8/1985 | Moore |
| 4,568,696 A | 2/1986 | Smerbeck et al. |
| 4,636,516 A | 1/1987 | Kuho et al. |
| 4,677,113 A | 6/1987 | Bell et al. |
| 4,708,966 A | 11/1987 | Loomans et al. |
| 4,711,903 A | 12/1987 | Mueller et al. |
| 4,714,776 A | 12/1987 | Bell et al. |
| 4,755,524 A | 7/1988 | Mueller et al. |
| 4,801,611 A | 1/1989 | Chinn et al. |
| 4,833,155 A | 5/1989 | Muchowski et al. |
| 4,835,190 A | 5/1989 | Mueller et al. |
| 4,849,428 A | 7/1989 | Dobson et al. |
| 4,857,588 A | 8/1989 | Coleman-Kammula |
| 4,906,662 A | 3/1990 | Hashimoto et al. |
| 4,935,440 A | 6/1990 | Muchowski et al. |
| 4,968,710 A | 11/1990 | Rustad |
| 4,985,465 A | 1/1991 | Hendler |
| 5,128,331 A | 7/1992 | Nguyen et al. |
| 5,143,928 A | 9/1992 | Cetenko et al. |
| 5,155,122 A | 10/1992 | Connor et al. |
| 5,234,937 A | 8/1993 | Capiris et al. |
| 5,237,070 A | 8/1993 | Scherrer |
| 5,248,682 A | 9/1993 | Connor et al. |
| 5,256,680 A | 10/1993 | Connor et al. |
| 5,280,045 A | 1/1994 | Dobson et al. |
| 5,290,800 A | 3/1994 | Cetenko et al. |
| 5,298,514 A | 3/1994 | Mueller et al. |
| 5,340,815 A | 8/1994 | Connor et al. |
| 5,342,838 A | 8/1994 | Mueller et al. |
| 5,347,036 A | 9/1994 | Scherrer |
| 5,356,898 A | 10/1994 | Belliotti et al. |
| 5,376,670 A | 12/1994 | Connor et al. |
| 5,487,893 A | 1/1996 | Vachy |
| 5,494,927 A | 2/1996 | Cetenko et al. |
| 5,495,043 A | 2/1996 | Scherrer |
| 5,498,745 A | 3/1996 | Scherrer |
| 5,510,361 A | 4/1996 | Scherz et al. |
| 5,527,824 A | 6/1996 | Scherrer |
| 5,612,321 A | 3/1997 | Nguyen |

(Continued)

FOREIGN PATENT DOCUMENTS

WO WO9105809 A1 5/1991
WO PCTUS200400811 10/2004

OTHER PUBLICATIONS

Blackshear, "Implantable Drug-Delivery System," Scientific American, vol. 241, No. 6, pp. 66-73, (Dec. 1979) (9 pages).
Orienti, et al., "Diffusion of Naproxen in Presence of β-Cyclodextrin Across a Silicone Rubber Membrane," Pharm. Acta Helv, 66, No. 7, pp. 204-208 (1991) (5 pages).
Bardin, "Implantable Contraception," Current Therapy in Endocrinology and Metabolism, pp. 263-270 (8 pages), vol. 5, 1994.
Li, et al., "An In-vitro Evaluation of Silicone Elastomer Latex for Topical Drug Delivery," Journal of Pharmacy and Pharmacology, 47, pp. 447-450 (1995) (4 pages).

(Continued)

*Primary Examiner*—Michael G Hartley
*Assistant Examiner*—Nissa M Westerberg
(74) *Attorney, Agent, or Firm*—Cox Smith Matthews Incorporated

(57) ABSTRACT

3,5-di-substituted-4-hydroxybenzylidene phosphonates and sulfonates useful in treating inflammatory disease, particularly osteoarthritis, and elastomeric particles for oral delivery of drugs are disclosed.

11 Claims, No Drawings

U.S. PATENT DOCUMENTS

| | | | |
|---|---|---|---|
| 5,700,451 | A | 12/1997 | Yue et al. |
| 5,709,847 | A | 1/1998 | Bissett et al. |
| 5,804,572 | A | 9/1998 | Blank et al. |
| 5,849,732 | A | 12/1998 | Suzuki et al. |
| 5,922,346 | A | 7/1999 | Hersh |
| 5,942,530 | A | 8/1999 | Panetta et al. |
| 6,153,226 | A | 11/2000 | Vachy et al. |
| 6,218,437 | B1 | 4/2001 | Chojkier |
| 6,348,493 | B1 | 2/2002 | Chojkier |
| 6,369,097 | B1 | 4/2002 | Chojkier |
| 6,420,428 | B1 | 7/2002 | Chojkier et al. |
| 6,455,547 | B1 | 9/2002 | Kis |

OTHER PUBLICATIONS

Mankin, Nonsteroidal Antinflammatory Drugs, Chapter Entitled "Normal Articular Cartilage and the Alterations in Osteoarthritis," a Wiley-Interscience Publication, p. 28 (1985) (2 pages).

Lazer, et al., "Antinflammatory 2.6, Di-tert-butyl-4-2 (2-arylethenyl)phenols," Journal of Medical Chem., 32, pp. 100-104 (1989) (5 pages).

Swingle, et al., "Anti-Inflammatory Activity of Antioxidants," Anti-Inflammatory and Anti-Rheumatic Drugs, vol. III, Chapter 4, CRC Press, Inc., pp. 105-126 (1985) (23 pages).

Moore, et al., "2,6 Di-tert-butyl-4-(2'-thenoyl)phenol(R-830): A novel nonsteroidal anti-inflammatory agent with antioxidant properties," Agents and Actions, vol. 12.5, pp. 674-683 (1982) (10 pages).

Isomura, et al., "Studies on the Synthesis and Anti-Inflammatory Activity of 2,6-Di-tert-butylphenols with a Heterocyclic Group at the 4-Position. I," Chem. Pharm. Bull., vol. 31, pp. 3168-3185 (1983) (18 pages).

Isomura, et al., "Synthesis and Anti-Inflammatory Activity of 2,6-Di-tert-butylphenols with a Heterocyclic Group at the 4-Position. III," Chem. Pharm. Bull., vol. 32, pp. 152-165 (1984) (14 pages).

Hidaka, et al., "Pharmacological Properties of a New Anti-Inflammatory Compound, $\alpha$-(3,5-Di-Tert-Butyl-4-Hydroxybenzylidene)-$\gamma$-Butyrolactone (KME-4), and its Inhibitory Effects on Prostaglandin Synthetase and 5-Lipoxygenase," Japan J. Pharmacol, 36, pp. 77-85 (1984) (9 pages).

Van Der Goot, et al., "The synthesis and anti-inflammatory activity of substituted 2-(4-hydroxyphenyl)-1,3-indandiones," Eur. J. Med. Chem., No. 5, pp. 425-428 (1978) (4 pages).

Katayama, et al., In vitro effect of N-methoxy-3-(3,5-ditert-butyl-4-hydroxy-benzylidene)-2-pyrrolidone (E-51 10), a novel nonsteroidal anti-inflammatory agent, on generation of some inflammatory mediators,: Agents and Actions, vol. 21, pp. 269-271 (1987) (3 pages).

Lazer, et al., "Effect of Structure on Potency and Selectivity in 2,6-Disubstituted 4-(2-Arylethenyl)phenol Lipoxgenase Inhibitors," J. Med. Chem., 33, pp. 1892-1898 (1990) (7 pages).

ANTI-INFLAMMATORY SUBSTITUTED PHENOLS AND ELASTOMERIC COMPOSITIONS FOR ORAL DELIVERY OF DRUGS

This application is being filed on 13 Jan. 2004, as a PCT International Patent application in the name of Adam Heller and Charles Haymore, both U.S. citizens, applicants for the designation of all countries.

Therapeutically useful phenols, phenol esters and phenol ethers, having bulky substituents in their 2 and 6 positions and a methylene group in their 4-position, the methylene group bound to a phosphonate or sulfonate anion, ester or amide are disclosed. The esters and amides are hydrolysable to phosphonates or sulfonates. The solubility of the calcium salts of the phosphonates or of the sulfonates in serum is less than 0.1 weight % at 37° C. Elastomer-comprising vehicles for oral drug delivery are also disclosed.

BACKGROUND OF THE INVENTION

The use of derivatives of 2,6-disubstituted phenols, such as 2,6-di-tert-butylphenols, as drugs is taught in the U.S. patents listed in Table 1. Their activity has been ascribed to inhibition of cyclooxidase (COX), or 5-lipooxygenase or leucotriene-oxidase. As anti-inflammatory drugs, they prevent, alleviate, cure, or are otherwise useful in treating animals, including humans, for pain, inflammatory disease, arthritic disease, rheumatoid arthritis, osteoarthritis, multiple sclerosis, inflammatory bowel disease, Crohn's disease, periodontal disease, gingivitis, conjunctivitis, fever, and sunburn. As antiviral drugs they prevent, alleviate, cure, or are otherwise they useful in treating hepatitis C, herpes, papilloma, warts, and other viral diseases. As anti-allergic drugs they prevent, alleviate, cure, or are otherwise useful in treating allergies, hay fever, poison ivy exposure, hypersensitivity, contact dermatitis, eczema, and asthma. As antilipidemics, they prevent, alleviate, cure, or are otherwise useful in treating atherosclerosis, high serum cholesterol, and cerebral stroke damage.

Nguyen U.S. Pat. No. 5,128,331 describes the lowering of plasma lipids and blood pressure by a di-phosphonate. The patents listed below in Table 1 disclose 2,6-di-substituted phenol-containing drugs and therapeutic uses. The papers listed below in Table 2 disclose anti-inflammatory 2,6-di-tert-butyl-4-(2-arylethenyl) phenols.

TABLE 1

| U.S. Pat. No. | Inventor | Assignee | Action or effect |
|---|---|---|---|
| 4,029,812 | Wagner | Dow Chemical | Hypolipidemic |
| 4,076,841 | Wagner | Dow Chemical | Hypolipidemic |
| 4,078,084 | Wagner | Dow Chemical | Hypolipidemic |
| 4,124,725 | Moore | Riker Labs | Anti-inflammatory |
| 4,172,082 | Moore | Riker Labs | Anti-inflammatory |
| 4,172,151 | Moore | Riker Labs | Anti-inflammatory |
| 4,212,882 | Moore | Riker Labs | Anti-inflammatory |
| 4,357,345 | Moore | Riker Labs | Anti-inflammatory |
| 4,414,217 | Moore | Riker Labs | Anti-inflammatory |
| 4,418,074 | Moore | Riker Labs | Anti-inflammatory |
| 4,431,831 | Moore | Riker Labs | Anti-inflammatory |
| 4,535,165 | Moore | Riker Labs | Anti-inflammatory |
| 4,568,696 | Smerbeck | Warner Lambert | Anti-inflammatory Leukotriene synthesis inhibitor. |
| 4,677,113 | Bell | Riker Labs | antiallergic |
| 4,636,516 | Kubo | Yamanouchi | Antiarthritic |
| 4,708,966 | Loomans | Procter & Gamble | Anti-inflammatory |
| 4,711,903 | Mueller | G. D. Searle | 5-lipooxygenase inhibitor |

TABLE 1-continued

| U.S. Pat. No. | Inventor | Assignee | Action or effect |
|---|---|---|---|
| 4,714,776 | Bell | Riker Labs | Antiallergic |
| 4,755,524 | Mueller | G. D. Searle | 5-lipooxygenase inhibitor |
| 4,833,155 | Muchowski | Syntex | Anti-inflammatory |
| 4,835,190 | Mueller | G. D. Searle | Anti-inflammatory & antiallergy |
| 4,849,428 | Dobson | Procter & Gamble | Anti-inflammatory |
| 4,857,588 | Mueller | G. D. Searle | 5-lipooxygenase inhibitor |
| 4,906,662 | Hashimoto | Otsuka Pharma | Anti-inflammatory, lipooxygenase inhibitor |
| 4,935,440 | Muchowski | Syntex | Anti-inflammatory |
| 4,968,710 | Rustad | Riker Labs | Antiallergic |
| 4,985,465 | Hendler | | Antiviral |
| 5,128,331 | Nguyen | Symphar | Hypolipidemic, lowering of blood pressure |
| 5,143,928 | Cetenko | Warner Lambert | Anti-inflammatory |
| 5,155,122 | Connor | Warner Lambert | Anti-inflammatory |
| 5,234,937 | Capiris | Warner Lambert | Anti-inflammatory |
| 5,237,070 | Scherrer | Warner Lambert | Anti-inflammatory |
| 5,248,682 | Connor | Warner Lambert | Anti-inflammatory |
| 5,256,680 | Connor | Warner Lambert | Anti-inflammatory |
| 5,280,045 | Dobson | Procter & Gamble | Anti-inflammatory |
| 5,290,800 | Cetenko | Warner Lambert | Anti-inflammatory |
| 5,298,514 | Mueller | G. D. Searle | Anti-inflammatory |
| 5,340,815 | Connor | Warner Lambert | Anti-inflammatory |
| 5,342,838 | Mueller | G. D. Searle | Anti-inflammatory |
| 5,347,036 | Scherrer | Riker Labs | Anti-inflammatory |
| 5,356,898 | Belliotti | Warner Lambert | Anti-inflammatory, antioxidant |
| 5,376,670 | Connor | Warner Lambert | Anti-inflammatory |
| 5,487,893 | Vachy | Fileco | Antiviral |
| 5,494,927 | Cetenko | Warner Lambert | Anti-inflammatory |
| 5,495,043 | Scherrer | Riker Labs | Antiallergic |
| 5,498,745 | Scherrer | Riker Labs | Antiallergic |
| 5,510,361 | Scherz | Procter & Gamble | Anti-inflammatory |
| 5,527,824 | Scherrer | Riker Labs | Leucotriene synthesase inhibitor |
| 5,612,321 | Nguyen | Hercules | Antiarthritic |
| 5,700,451 | Yue | Procter & Gamble | Sunscreen |
| 5,709,847 | Bissett | Procter & Gamble | Sunscreen |
| 5,804,572 | Blank | Procter & Gamble | Anti-wrinkle, skin atrophy prevention |
| 5,849,732 | Suzuki | Tanabe Seiyaku | Antioxidant preventing heart attacks |
| 5,942,530 | Panetta | Eli Lilly | Pain treatment |
| 6,153,226 | Vachy | Fileco | Antiviral |
| 6,218,437 | Chojkier | U. California | Anti-hepatitis C |
| 6,348,493 | Chojkier | U. California | Anti-hepatitis C |
| 6,369,097 | Chojkier | U. California | Anti-hepatitis C |
| 6,420,428 | Chojkier | U. California | Anti-hepatitis C |

TABLE 2

Lazer et al., J. Med. Chem., 1989, 32, pp. 100-104
K. F. Swingle et al. In: "Anti-inflammatory and Anti-rheumatic Drugs"
K. D. Rainsford, editor, CRC Press, 1985, pp. 105-126,
"Anti-inflammatory activity of antioxidants"
Moore & Swingle, Agents & Actions, 12 (5): 674-683 (1982)
Hidaka et al. Ensho 3 (4): 511-512 (1983)
Isomura et al., Chem. Pharm. Bull., 31 (9): 3168-3185 (1983)
Isomura et al., Chem. Pharm. Bull., 32 (1): 152-165 (1984); Noda et al., Kokai 80/15, 460
Katsumi et al., "Pharmacological Properties of a New Anti-inflammatory Compound, α-(3,5-di-tertbutyl-4-hydroxybenzylidene)-γ-butyrolactone (KME-4) and its Inhibitory Effects on Prostaglandin Synthetase and 5-lipooxygenase, Jpn. J. Pharmacol. 36 (1), 77-85 (1984)
VanDerGoot et al., European J. Medicinal Chem., 13 (5) 425-428
Katayama et al., "In-vitro effect of N-methoxy-3-(3,5-ditert-butyl-4-hydroxy-benzylidene)-2-pyrrolidone (E-5110), a novel non-steroidal anti-inflammatory agent, on generation of some inflammatory mediators" Agents and Action, 21, 269-271 (1987)

TABLE 2-continued

Lazer et al. "Effect of Structure on Potency and Selectivity in 2,6-Disubstituted 4-(2-Arylethenyl)-phenol Lipooxygenase Inhibitors J. Med. Chem. 33, 1982-1998 (1990).

The 2,6-disubstituted phenols, such as 2,6-di-tert-butylphenols are useful also as antioxidants and are used as stabilizing additives in plastics, elastomers, waxes and oils. Compound 1, the calcium salt of the monoethyl ester of (((3,5-bis(1,1-dimethylethyl)-4-hydroxyphenyl)methyl) phosphonic acid, is an antioxidant sold, for example, by Ciba® Specialty Chemicals as Irganox® 1425. It is described by Ciba® Specialty Chemicals as a "highly efficient, non-discoloring stabilizer for organic substrates such as plastics, synthetic fibers, elastomers, adhesives, waxes, oils and fats. It protects these substrates against thermo-oxidative degradation. It is odorless, stable to light, and has excellent color retention. It has good compatibility with most substrates and high resistance to extraction" (by water or organic solvents). Furthermore, according to Ciba® Specialty Chemicals, Compound 1 imparts processing and good long term stability to polyolefins. It is particularly suitable for use in polypropylene fibers. Compound 1 is also an effective stabilizer for polyesters, crosslinked elastomers, specialty adhesives, and natural and synthetic tackifier resins and is additionally used as an esterification catalyst for the preparation of rosin esters. It is recommended for applications requiring improved extraction resistance, low volatility, excellent color and color stability and superior gas-fading resistance." Its solubility in water is reported to be <0.01 weight %. In the rat, the oral LD50 of Compound 1 exceeds 6000 mg/kg and in the Chinese hamster it exceeds 2000 mg/kg. Its 4 hour inhalation at >2.35 mg/l air aerosol, with exposure to an aerosol comprising mostly (~80%) particles smaller than 7 μm, resulted in no deaths of rats. Its intraperitoneal LD 50 in the rat is 662 mg/kg. No bioconcentration (accumulation) was detected in carp at 0.3-3 ppm.

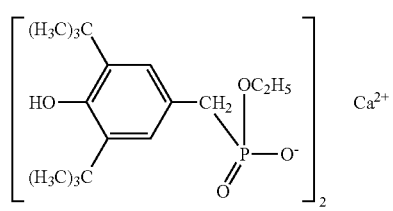

Compound 1

SUMMARY OF THE INVENTION

The invention provides compounds of the family shown as Structure 1, referred to herein as the "anti-inflammatory structure." The compounds of the invention are useful drugs for treating diseases, particularly inflammatory diseases, including arthritic diseases, such as inflammations of joints, osteoarthritis, or Crohn's disease. In these compounds, R can be H, or an ester-forming group such as acetyl ($CH_3CO-$) or benzoyl, or an ether-forming group such as methyl, ethyl, or lactate. $R_1$ and $R_2$ are bulky groups. The bulky groups can be identical or

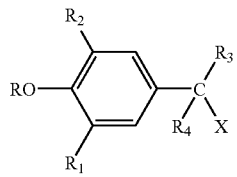

Structure 1 non-identical, and can be a group containing a ring-bound tertiary carbon atom, such as that of the tert-butyl group in Compound 1, or that of the trifluoromethyl group, or it can be a trialkylsilyl group, such as a trimethylsilyl group. X contains phosphorus or sulfur, and is preferably a phosphonic or sulfonic acid, or a salt of these acids, or an ester of these acids, or an amide of these acids. The solubility of the calcium salts of the phosphonic or sulfonic acids in water at 37° C. between pH 7.2 and 7.4 and at the normal physiological concentration of dissolved calcium cations in serum is less than 0.1 weight % and preferably less than 0.01 weight %. The concentration of the dissolved or protein-bound biologically active phosphonate or sulfonate increases, however, when the local concentration of a calcium ion binding or precipitating anion is increased. It is known that the concentrations of some calcium binding or precipitating anions are higher in inflamed and/or arthritic tissues than in normal tissues.

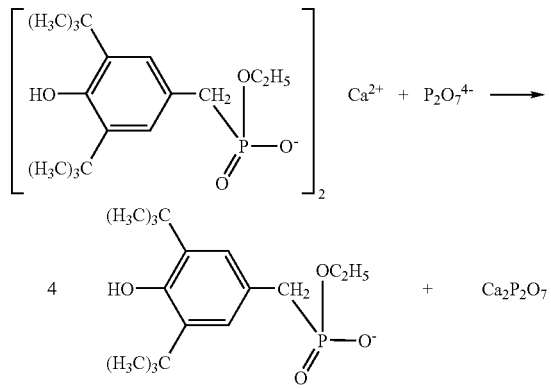

Anions, the concentrations of which are higher in arthritic or inflamed tissues, are exemplified by di-, tri-, and polyphosphates and are specifically exemplified by pyrophosphate. The higher concentration of pyrophosphate, such as $H_2P_2O_7^{2-}$, in the arthritic tissue is known to cause the accumulation of insoluble calcium pyrophosphate, such as $Ca_2P_2O_7$, containing matter in osteoarthritic tissues and in arthritic joints, where pyrophosphate is generated or released and is precipitated as a calcium salt. Because the pyrophosphate or other calcium binding agent reacts with the calcium salt of the anti-arthritic drug, exemplified by Compound 1, according to a reaction such as the above-shown calcium pyrophosphate precipitating reaction, the soluble anion of the anti-arthritic or analgesic drug is locally released. Local release provides for an adequate therapeutic concentration of the drug in the diseased tissue, while its systemic concentration remains low enough to avoid undesired effects that would result if tissues other than the diseased tissue were exposed to the damagingly high concentrations of the anion. Thus the recognized damage to parts of the digestive system, the kidneys and the skin caused by anti-arthritic, anti-inflammatory and analgesic drugs is alleviated or altogether avoided.

These and other drugs can be delivered orally in small particles of elastomers, or in capsules or tablets comprising small particles of elastomers, in which the drugs are dispersed or dissolved. Although the drug can be added to the particles of the elastomer by soaking the particles in a solution of the drug, it is preferred to add the drug before or while the elastomer is being compounded. The elastomer can be any non-toxic rubber or elastomer. Examples include elastomers comprising silicones, polydienes, polyolefins, and copolymers of styrene and butadiene.

DETAILED DESCRIPTION OF THE INVENTION

Compounds

Useful compounds of the invention contain the "anti-inflamatory structure" shown below as Structure 1.

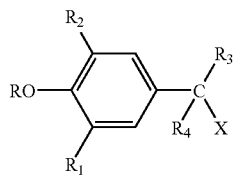

Stucture 1

In the anti-inflammatory Structure 1, X=P or S phosphonic or sulfonic acid, or salt, ester, or amide thereof, or a phosphonate or sulfonate ion; R=H, or ester-forming group (acetyl, benzoyl), or ether-forming group (methyl, ethyl, lactate); and $R_1$, $R_2$ = bulky groups such as ring-bound tertiary C (tert-butyl; trifluromethyl; trialkylsilyl (trimethylsilyl)) (—C$(CH_3)_3$,—$CF_3$,—$Si(CH_3)_3$) or -methylcyclohexyl; $R_3$, $R_4$=—H, —F, or —CH3.

Useful compounds of the invention are phosphonates or sulfonates or their precursors, the solubility of the calcium salts of which in serum at 37° C. is less than 0.1 weight %, preferably less than 0.01 weight %, comprising the anti-inflammatory structure. They are exemplified by the phenols or phenol esters, or phenol ethers of Structure 1. Preferred are phenols and phenol esters that can be hydrolyzed in the digestive system. Examples of the phenol esters are acetate, lactate and pyruvate esters.

The phenols are substituted in their 2 and 6 positions with bulky functions $R_1$ and $R_2$. The preferred bulky substituent is the tertiary butyl function —C $(CH_3)_3$, its tri-alkylated carbon bound to the ring. Other examples of such bulky functions are —$Si(CH_3)_3$ and —$CF_3$. In general, it is preferred that the ring-bound carbon atoms of the bulky functions be tertiary carbon atoms, meaning that their neighboring atoms, opposite their ring side, not be hydrogens, but carbon or oxygen or sulfur or nitrogen. Thus phenols where $R_1$ or $R_2$ is 1-methylcyclohexyl are useful. While the ring bound atoms in the 2 and 6 positions of the phenols are preferably carbon atoms, as are the atoms next to the ring bound carbons, the atoms further removed from the aromatic ring can be nitrogen, oxygen or sulfur. The group in position 4, para to the OH of the phenol, is —C($R_3R_4$)X, where $R_3$ and $R_4$ can be identical or different. $R_3$ and $R_4$ are chosen from the group hydrogen, fluorine or methyl. X is, or comprises, at neutral pH, a phosphonate or a sulfonate anion, or is a compound forming upon its hydrolysis a phosphonate or sulfonate anion, such as an amide or an ester. The preferred group in position 4 is —$CH_2X$, where X is or comprises at neutral pH, a phosphonate or a sulfonate anion, or is a compound forming upon its hydrolysis a phosphonate or sulfonate anion, such as an amide or an ester. Thus, X is a phosphonate or a phosphonate precursor, yielding upon hydrolysis a phosphonate, exemplified by functions 3, 4, and 5 or a phosphamide. Alternatively, is a sulfonate or sulfonate precursor, yielding upon hydrolysis a sulfonate. The salts can be of any non-toxic organic or inorganic cation, such as choline, ammonium, lysine, $Na^+$, $K^+$, $Ca^{2+}$, $Mg^{2+}$, $Li^+$, or $Zn^{2+}$.

Function 3

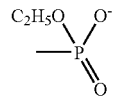

Function 4

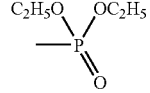

Function 5

While the ethyl esters are shown in functions 4 and 5, the esters can be of other alcohols, for example, of butyl alcohol, isopropyl alcohol, ethylene glycol, glycerol, glucose, and other sugars. For function 5, the two alcohols can be similar or can differ. With diols or triols, or with sugars, the diesters can be cyclic, as shown in Function 6 for glycerol. Other examples of the group in the 4 position of the phenol include sulfonates (Function 7) and hydrolysable, sulfonate precursors, such as the esters of Function 8 and the amides of Function 9. While the ethyl ester is shown in Function 8, it can be an ester of another alcohol, for example, those listed above.

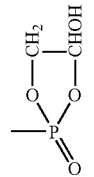

Funciton 6

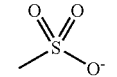

Function 7

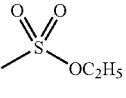

Function 8

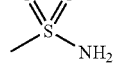

Function 9

Examples of the cations in the salts of Function 7 are those mentioned for the phosphonates and examples of the alcohols in Function 8 are those listed for the phosphonate esters. The amides of Function 9 can be monoalkyl or dialkylamides, the nitrogen bound hydrogen atoms being replaced by groups such as $CH_3$, $C_2H_5$ or cyclohexyl. The groups can be cyclic or heterocyclic. The most preferred compounds are the Function 4 phosphonate esters and Function 3 salts of Compound 1.

Other useful compounds would include, for example, Compound 2, an analog of 16-hydroxyeicosatetraenoic acid and an inhibitor of leukotriene production in a neutrophils according to J. R Falck et al. PCT Int. Appl. (1999), WO 9959964 A1 19991125 Application: WO 99-US10728 19990514

Compound 2

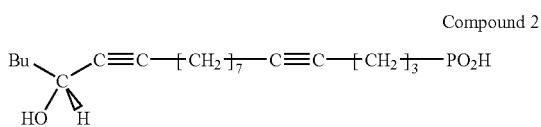

Although the subject compounds of this invention can be administered or applied by any method of drug administration, for example, by injection in the arthritic tissue or elsewhere, or rectally, or in a salve applied to the skin, the preferred method is oral administration of capsules or tablets. The daily dosage is about 1 microgram/kg to about 100 mg/kg, the preferred dosage being about 0.01 mg/kg to about 10 mg/kg.

While not wishing to be bound by any theory, a feature of the phosphonate and sulfonate anions, particularly the preferred phosphonate anions, is their binding with partially or fully hydrated cations having a charge greater than one, such as $Ca^{2+}$, $Mg^{2+}$, $Fe^{2+}$, or $Zn^{2+}$. Upon binding with $Ca^{2+}$, the phosphonates displace water molecules solvating the $Ca^{2+}$, cation, neutralize or reverse its positive charge, forming a salt that is substantially insoluble at or near the physiological pH, temperature, and $Ca^{2+}$ ion concentration. Because they bind hydrated or partially hydrated $Ca^{2+}$, the drugs of the anti-inflammatory structure can accumulate where hydrated $Ca^{2+}$ abounds, for example at surfaces of bones and in calcified arthritic cartilage, symptomatic in *condrochalcinosis articularis*. Because in the osteoarthritic joint the concentrations of $Ca^{2+}$-binding ligands, such as pyrophosphate, is increased, and the concentrations of di-, tri-, or poly-phosphates exemplified by calcium ion binding nucleotide mono, di-, and tri-phosphates, DNA, RNA and their degradation products may be increased, the concentration of the dissolved and biologically active phosphonate or sulfonate ion can be locally high, even though the systemic concentration is low. The high concentration of the drug at the site where it is needed and its much lower concentration where it is not needed can reduce the well-known complications and side effects of treatments by the anti-inflammatory drug. Specifically, gastric and duodenal ulcers, hepatic injury, renal toxicity, lower bowel toxicity, and cutaneous toxicity caused by or associated with the use of non-steroidal anti-inflammatory drugs could be avoided. The increase in the local concentration of the dissolved phosphonate or sulfonate could result, for example, from the shifting of the equilibria such as whereby the soluble anion is released from its insoluble calcium salt. Increase in the pyrophosphate concentration in the osteoarthritic joint has been reported, for example by Henry J. Mankin of the Orthopedic Research Laboratories of Massachusetts General Hospital and Harvard Medical School in the Chapter "*Normal Articular Cartilage and the Alterations in Osteoarthritis*" in the book "*Nonsteroidal Antiinflammatory Drugs*", Joseph G. Lombardino, Ed., Wiley, New York, 1985, page 28.

Usually it is preferred that the solubility of the $Ca^{2+}$ salt of the phosphonate or the sulfonate administered or formed of the administered compound be less that 0.1 weight-% in water at pH 7.2 at 37° C. at the physiological $Ca^{2+}$ concentration in serum; and it is most preferred that the solubility under these conditions be less than about 0.01 weight-%.

While the hindered phenols, such as Compound 1, are examples of a family of compounds with anti-inflammatory structures, other anti-inflammatory structural element-comprising phosphonates and sulfonates, having similarly insoluble calcium salts, can be used for treatment of the inflammatory disease exemplified by osteoarthritis.

Another useful phosphonate is Compound 2, an analog of 16-hydroxyeicosatetraenoic acid and an inhibitor of leukotriene production in neutrophils, according to J. R Falck et al. PCT Int. Appl. (1999), WO 9959964 A1 19991125.

Oral Drug Delivery Using Elastomeric Vehicles:

The diffusion coefficients and the solubilities of organic solvent-soluble compounds are, in general, higher in elastomers than they are in other polymers. This has made them useful materials in drug delivering implants, particularly in subcutaneous implants and in drug delivering patches worn on the skin. Organic soluble compounds are compounds that are more soluble in at least one organic solvent than they are in water, are preferably at lest ten times more soluble in an organic solvent than they are in water and, are most preferably at least one hundred times more soluble in an organic solvent than they are in water.

The most widely used elastomeric implant materials are elastomeric silicones and polyurethanes. Their use in drug delivering implants has been described, for example, by Blackshear, 1979, "Implantable drug-delivery systems," *Scientific American,* 241(6): 66-73; Orienti et al., 1991, "Diffusion of naproxen in presence of β-cyclodextrin across a silicone rubber membrane," *Pharmaceutica Acta Helvetiae,* 66(7): 204-8; Szycher, "Hydrophilic polyurethane elastomers for drug delivery systems," PCT Int. Appl. WO 9105809 A1 19910502; Bardin, 1994, "Implantable contraception," *Current Therapy in Endocrinology and Metabolism,* 5: 263-70; and Li et al., 1995, "An in-vitro evaluation of silicone elastomer latex for topical drug delivery," *Journal of Pharmacy and Pharmacology,* 47(6): 47-50.

Compound 1

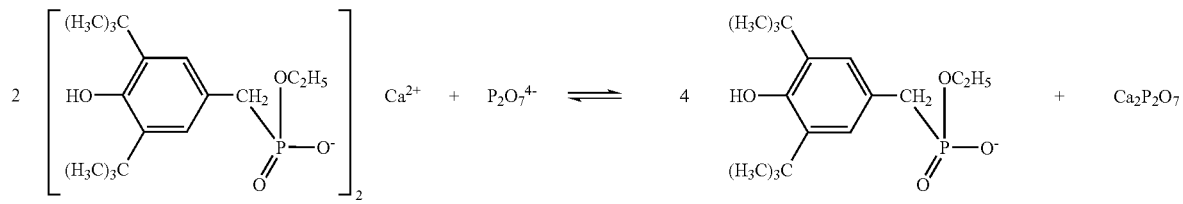

Elastomers are described herein as useful vehicles for oral drug delivery. The drug is dissolved, or dissolved and dispersed, in the elastomer. Unlike in implants, biocompatibility of the elastomers is not of essence for oral drug delivery. In addition to the elastomeric silicones and polyurethanes, elastomeric materials of which non-toxic rubber products are made can also be used. They include, for example, elastomers made of polymers or copolymers of styrene and butadiene, cis-isoprene, chlorinated butadiene, or olefins. The polymers and co-polymers that are precursors of the preferred elastomers are preferably crosslinked or vulcanized to improve their mechanical strength, to reduce or prevent their adhesion to surfaces, and to prevent or reduce their dissolution in solvents. The elastomer in the particles is preferably vulcanized or crosslinked.

The elastomer particles are taken orally either as such, or encapsulated in a readily dissolved gelatin or other capsule. They pass the digestive system and are excreted without substantially changing their shape.

Tires are an example of a drug-containing vulcanized elastomer. Examples of drugs contained in tires include antioxidants added prior to vulcanization in the compounding of rubbers in the manufacture of tires. They are exemplified by added, or in-situ formed, 2,6-di-tert-butylphenol derivatives, constituting 1-3 weight % of the tires. As seen in Examples 10, 11, 13, and 14, orally-administered drug-comprising elastomers are effective in treating disease in animals. Useful elastomer particles are larger than about 0.001 cm in diameter and smaller than about 1 cm in diameter; preferred particles are larger than about 0.01 cm in diameter and smaller than about 0.5 cm diameter; most preferred particles are larger than about 0.05 and smaller than about 0.4 cm diameter. The elastomer particles, in which the drug is preferably homogeneously distributed, can have any shape. The drug can be dissolved or dispersed in the particles. It is preferred that at least 1 weight-% of the drug contained in the particles be dissolved rather than dispersed, and it is most preferred that at least 10 weight-% of the drug be dissolved. The preferred particles can have hollow domains; however, the preferred volume fraction of the hollow domains is less than 10 volume-%. When the particles are non-spherical, the above diameters represent their longest dimension.

The particles can comprise any non-toxic elastomer, vulcanized or crosslinked elastomers being preferred. The preferred particles are insoluble in the fluids of the digestive system and are excreted without change in their shape. After passing the digestive system, the weight of the particles decreases preferably by less than about the weight of the drug carried by the particles. The drug content of the elastomeric particles is greater than about 0.001 weight-% and is less than about 20 weight-%; it is preferably greater than about 0.01 weight-% and less than about 10 weight-%; most preferably it is greater than about 0.03 weight-% and less than about 3 weight-%. A therapeutically useful weight of the drug containing elastomeric particles is administered orally. The preferred weight of the daily ingested particles during the period of therapy is between about 0.1 g and about 30 g, and the most preferred weight is between about 0.5 g and about 10 g.

The distance to which the drug diffuses in the elastomer during the period between the oral intake of the particles and their excretion is termed herein the "diffusion length." Elastomeric particles passing the digestive system release some or all of the therapeutic agent before their excretion. The elastomeric particles can be designed so that all of their therapeutically active ingredient is released in a period shorter than the period between their oral intake and excretion. This is done by making the dimensions of the particles small relative to the diffusion length of the active ingredient in the elastomer. Alternatively, the particles can be designed so that only a fraction of their active ingredient is extracted in the period of passage through the digestive system. This is done by making the dimensions of the particles large relative to the diffusion length of the active ingredient in the elastomer. In general, it is preferred to tailor the diffusion length of the active ingredient and the dimensions of the ingested particles so that all, or only a fraction of, the active ingredient is released in the period between the oral intake of the particles and their excretion. The preferred extracted fraction in the period of passage through the digestive system is greater than 0.001 and smaller than 0.99; the most preferred fraction is greater than 0.01 and smaller than 0.8. Because the period between the oral intake of the particles and their excretion can vary, it is preferred to use the elastomeric particles when bowel movements are regular. When the period between ingestion and excretion is shorter than normal, for example in case of diarrhea, the amount ingested can be increased; when the period is longer, for example in case of constipation, the amount can be decreased. It is preferred to label the therapeutic composition made with the elastomeric particles with a statement such as "for regular bowel movement". It is also preferred to label the therapeutic matter with warnings against usage in case of irregular bowel movement, such as in cases of diarrhea or constipation or to appropriately label compositions designed to treat these special situations.

The elastomeric particles can be used as vehicles for any drug that is soluble in the elastomer and diffuses in the elastomer. The solubility of the drug in the elastomer is greater than about 0.001 weight-%, preferably greater than about 0.01 weight % and most preferably greater than 0.1 weight-%.

Examples of applications are treatment of inflammatory diseases of the digestive tract, such as Crohn's disease, where the passing particles may provide elevated drug concentrations at the inflamed tissue. Other examples are treatment of arthritis, such as osteoarthritis. Examples of the active components of drugs in the elastomeric vehicle include those of this application and those described in its cited references, listed in part in Table 1 and the novel drugs disclosed in this application.

EXAMPLES

In this application "rubber" and "elastomer" have the same meaning. The meanings of the terms "tires", "ground tires" and "ground rubber tires" are the same. The latter terms mean rubber tires that were ground to particles of about 1/16 inch to about 1/8 inch average diameter. In the following studies, dogs received with their daily meal one tablespoonful of ground tires for four weeks. Ground tires were administered to 8 dogs diagnosed with arthritis or chronic or degenerative joint disease. The condition of 5 dogs did not improve. The Examples below describe 3 dogs in which improvement was evident. Compound 1 was administered to 5 dogs with arthritis or chronic or degenerative joint disease. The Examples below describe 4 dogs for which improvement was evident.

Example 1

Compounding of Elastomers with Antioxidants and Their Grinding to Small Particles The base material, SBR rubber Duradene 706 (Firestone Polymers, Akron, Ohio) was in the form of a 75 lb block termed "bale". SBR rubber is an elastomeric copolymer of styrene and butadiene, or an elastomeric copolymer formed mostly of styrene and butadiene. The Duradene 706 bale was sheared to blocks of about 1 inch×4 inches×12 inches that were placed in a roller mill. The roller mill had two 14 inch diameter rollers, rolling in opposite directions. As a result of the rolling, the sheared blocks of rubber were spread, covering about the entire surface of the rollers. At the point where the rubber was "banded", meaning that the rubber covered the circumference of the rollers on the roller mill, the additives were spread and well mixed with the rubber. The weight percentages (wt %) of materials in the banded mixture were 1.8 wt % stearic acid; 1.8 wt % of either Compound 1 or 2,6-di-tert-butyl-4-methylphenol (from

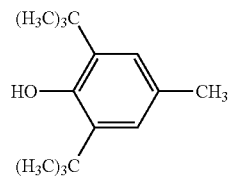

2,6-di-tert-butyl-4-methylphenol

Aldrich, Milwaukee, Wis.) ; 0.9 wt % of zinc oxide; 1.35-wt % tetramethylthiuram disulfide; 1.8-wt % sulfur; and 92.35 wt % of Duradene 706. After the ingredients were thoroughly mixed, the banded rubber sheets were heated for 15 minutes to 320° F. to crosslink the elastomer by its vulcanization, then allowed to cool to ambient temperature and ground, using an extrusion grinder # 4625 at about 4,900 rpm, to particles having a diameter in the range of about 1/16 inch to about 1/8 inch.

Examples 2 through 14

Methodology

The experiments below were performed on dogs after the informed consent of their owners was obtained. The owners did not know whether their dog was receiving the drug candidate or a placebo. The specified compound was administered orally once a day with the dog's meal. A control group, receiving a placebo, was given ground dry dog food of similar particle size. The owners reported weekly any change in the ability of their dog to stand up, walk, run, climb and descend stairs, get on and off a bed, sofa, or chair, get into and out of a car, their limping and behavior.

Examples 2-6

Placebos

In these examples the dogs were given as a daily oral dose for 4 weeks, 1 tablespoonful of the placebo. In Example 3 the dog was a 12 year old male Pug weighing 24 lbs; in Example 4, it was a 13 year old male Scooter weighing 19 lbs; in Example 5, it was a 10 year old male Australian Cattle mix weighing 28 lbs; in Example 6, it was a 10 year old male Sheltie weighing 43 lbs; in Example 7, it was a 13 year old male Golden Retriever weighing 58 lbs. In each of the placebo controls there was no physical improvement, except that two of the owners reported that their dog appeared initially "slightly perkier".

Example 7

Effectiveness of Compound 1 Versus the Placebo

A 33 lb 11 year old male Kelpie-mix having arthritis in the shoulders and in the elbow had difficulty getting down stairs, bed, sofa, or out of a car. The dog was given orally 1 tablespoonful of the placebo daily with its meal for four weeks. The condition of the dog did not change. In the next four-week period the dog was given daily one gelatin capsule containing about 10 mg of Compound 1. After 1 week the dog got down the sofa and out of the car more easily. After 2 weeks it moved smoothly, had less difficulty getting out of the car or off the sofa, ran better and more often, and was more active. After 3 weeks, it was freely getting off the bed, down from the sofa and out of the car. In the $4^{th}$ week, the dog's condition continued to improve.

Example 8

Effectiveness of Compound 1 Versus the Placebo

A 13-lb 15-year-old spayed female miniature Poodle had an unknown disease making it difficult for it to climb stairs, jump, climb, or run; causing it to limp when first getting out of her bed in the morning. The dog was given daily for four weeks 1 flat tablespoonful of the placebo. There was no change, other than the dog being more active, which the owner attributed to cooler weather. After 3 months of no treatment, the dog was given daily one gelatin capsule containing about 10 mg of Compound 1 for 4 weeks. After two weeks the dog climbed stairs with less hesitation and ran occasionally. After 3 weeks, it ran frequently and jumped up on the sofa without hesitation. After 4 weeks it was climbing and running freely.

Example 9

Effectiveness of Compound 1 Versus Rimadyl®

An 85 lb 12-year-old female Labrador retriever was diagnosed as suffering of arthritis of the hips. The dog had severe difficulty standing up and was not running. The dog was treated with Rimadyl®, which slightly improved the dog's condition. The dog was then given daily one gelatin capsule containing about 15 mg of Compound 1 and Rimadyl®. After 1 week of taking Compound 1, the dog stood up without assistance and limped less. After two weeks the dog moved faster and was not bothered by its hips. After 3 weeks, it started to move faster, then to run and the Rimadyl® was discontinued. In the 4th week of treatment with Compound 1, the dog got up and moved rapidly with ease and it's running improved.

Example 10

Effectiveness of Rubber Particles Compounded with Compound 1

A 32 lb 12 year old male Cocker spaniel was diagnosed as suffering from arthritis of the right knee. The dog had surgery a year earlier on this knee. The dog could not jump up and down on the owner's bed or into the car of the owner. After the dog was given daily for 4 weeks one gelatin capsule containing about 200 mg of the rubber compounded, as described in Example 1, with Compound 1, the dog regained its ability to freely jump up and down the bed and into the car.

Example 11

Effectiveness of Ground Tires and of Compound 1

A 62-lb 13½-year-old male Australian cattle dog was diagnosed as suffering from arthritis. The dog had difficulty standing and stood only for short periods; could walk only short distances, limped, climbed only one or two stairs a day, and did not run. The dog was first given daily orally for 4 weeks, 1 level tablespoonful of ground rubber tires having a particle size of about 1/16 inch to about 1/8 inch. After 1 week, the dog limped slightly less. In the second week, the dog, for the first time in several years, jumped off the bed without showing signs of distress; in the third week it got up and walked; in the 4$^{th}$ week, again for the first time in year, it jumped out of the car instead of waiting to be lifted out.

The dog was not treated for the next 5 months. After this period, the dog could get up without assistance, stand for only a brief time, walk only a short distance and climb only two steps. The treatment of the dog then was resumed, this time with Compound 1. The dog was given daily, one gelatin capsule containing about 10 mg of Compound 1 for 4 weeks. After one week the dog stood longer, walked, and enjoyed the outdoors; after 2 weeks, the dog stood well, limped less, and climbed the 3 stairs to and from the house; after 3 weeks it trotted and climbed 5 stairs; after 4 weeks its condition was further improved.

Example 12

Ineffectiveness of the Rubber Compounded with 2,6-di-tert-butyl4-methylphenol

A 13.5 year old 80 lb male Samoyed, having difficulty in getting up and limping because of back hip arthritis, was given daily orally 1 tablespoonful of the placebo for a period of four weeks. There was no change in its condition. Next, the dog was given 1 tablespoonful of the elastomer of Example 1, made with of 2,6-di-tert-butyl-4-methylphenol. There was no change in the condition of the dog.

Example 13

Effectiveness of Ground Tires

A five-year-old 82 lb female Rottweiler had trouble getting into position to defecate, getting up and lying down, and going on hikes because of arthritis and hip dysplasia. A veterinarian characterized its hip x-rays as the "worst she had seen." The dog was given daily one tablespoonful of ground tires for four weeks. In the first week, the owner noticed a "dramatic difference". The dog was getting up with ease, ran around, and went hiking with the owner. After two weeks, the dog jumped into the owner's truck, after not doing this since the dog was young. The arthritis and hip dysplasia symptoms of the dog disappeared after four weeks.

Example 14

Effectiveness of Ground Tires

A 10 year old female black Labrador weighing 101 lbs was diagnosed as having arthritis and possibly dysplasia of the hips, causing the dog to limp, and making it hard for the dog to run for more than 1 to 20 minutes, or to go up and down stairs. The dog was given one tablespoonful of ground tires for four weeks. Within the 4-week treatment period, the dog stopped limping, was able to go up and down stairs, and regained its ability to run for an extended period.

We claim:

1. A method of treating arthritis in a subject comprising administering to the subject a compound comprising the structure of Formula I:

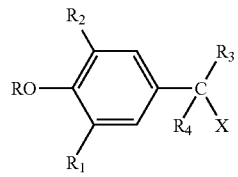

Formula I where:
X is a phosphonate or sulfonate ion, or an acid, salt, ester, or amide thereof;
R is H, an alkyl group, or an alkyl group connected to a carbonyl group;
$R_1$ and $R_2$ are the same or different, and are groups comprising a ring-bound tertiary carbon atom; and
$R_3$ and $R_4$ are the same or different, and are H, F, or $CH_3$.

2. The method of claim 1, wherein a calcium salt of the said phosphonate or sulfonate ion has a solubility in animal serum at physiological temperature, pH, and $Ca^{2+}$ concentration, of less than 0.1 weight-%.

3. The method of claim 2, wherein said solubility is less than 0.01 weight-%.

4. The method of claim 1, wherein X is a phosphonate ion, or an acid, salt ester or amide thereof.

5. The method of claim 1, where said compound, upon hydrolysis in said subject, forms a phosphonate ion.

6. The method of claim 1, wherein said compound comprises the chemical structure:

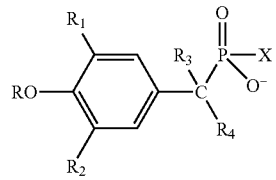

where:
R is H, an alkyl group, an aryl group, a phenol group connected to a carbonyl group or a lactyl group;
$R_1$ and $R_2$ are the same or different, and are groups comprising a tertiary carbon atom bound to the ring, tert-butyl, trimethyisilyl, or trifluoromethyl;
$R_3$ and $R_4$ are the same or different, and are hydrogen, fluorine, or methyl; and
X is a nitrogen atom or an oxygen atom.

7. The method of claim 6, wherein the compound is a phosphonate, or is hydrolyzed to a phosponate in vivo.

8. The method of claim 1, wherein the compound comprises the acid:

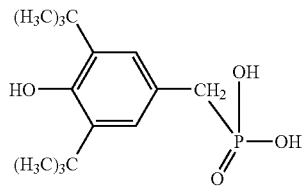

or a salt, ester, or amide thereof.

9. The method of claim 1, wherein said compound comprises the anion:

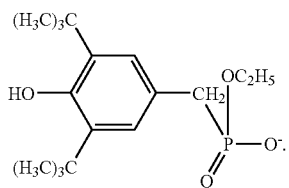

10. A method of treating arthritis in a subject comprising administering to the subject a compound comprising the structure:

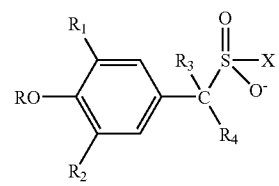

where:
R is H, an alkyl group, an aryl group, a phenol group connected to a carbonyl group or a lactyl group;
$R_1$ and $R_2$ are the same or different, and are groups comprising a tertiary carbon atom bound to the ring, tert-butyl, trimiethylsilyl, or trifluoromethyl;
$R_3$ and $R_4$ are the same or different, and are hydrogen, fluorine, or methyl; and
X is a nitrogen atom or an oxygen atom.

11. The method of claim 10, wherein the compound is a sulfonate, or is hydrolyzed to a sulfonate in vivo.

* * * * *